United States Patent [19]

Crystal et al.

[11] Patent Number: 5,869,037
[45] Date of Patent: Feb. 9, 1999

[54] ADENOVIRAL-MEDIATED GENE TRANSFER TO ADIPOCYTES

[75] Inventors: Ronald G. Crystal, Potomac, Md.; Christopher J. Magovern, New York, N.Y.

[73] Assignee: Cornell Research Foundation, Inc., Ithaca, N.Y.

[21] Appl. No.: 672,461

[22] Filed: Jun. 26, 1996

[51] Int. Cl.[6] .......................... A61K 35/12; A61K 48/00; C12N 15/09; C12N 15/86

[52] U.S. Cl. .................. 424/93.2; 424/93.7; 424/93.21; 435/325; 435/320.1; 435/172.3; 514/44

[58] Field of Search ...................... 514/2, 44; 435/172.3, 435/320.1, 252.3, 325.1; 424/93.21, 93.7, 93.2; 536/24.1

[56] References Cited

U.S. PATENT DOCUMENTS

| | | | |
|---|---|---|---|
| 5,268,295 | 12/1993 | Serrero | 435/252.3 |
| 5,318,957 | 6/1994 | Cid et al. | 514/8 |
| 5,399,346 | 3/1995 | Anderson et al. | 424/93 |
| 5,453,270 | 9/1995 | Bills et al. | 424/93.7 |
| 5,476,926 | 12/1995 | Spiegelman et al. | 536/24.1 |
| 5,652,225 | 7/1997 | Isner et al. | 514/44 |

FOREIGN PATENT DOCUMENTS

| | | |
|---|---|---|
| 518389 | 12/1992 | European Pat. Off. . |
| 2292382 | 2/1996 | United Kingdom . |
| WO92/09616 | 6/1992 | WIPO . |
| WO95/11984 | 5/1995 | WIPO . |
| WO95/19434 | 7/1995 | WIPO . |
| WO96/40172 | 12/1996 | WIPO . |

OTHER PUBLICATIONS

Crescenzi et al. (J. Cellular Physiology, 1995 Jan 162 (1) 26–35). Abstract Only.
Marshal, Science, 269:1050–1055, 1995.
Miller et al., FASEB J. 9:190–199, 1995.
Culver et al., Trends Genetics 10(5):174–178, 1994.
Hodgson, Exp. Opin. Ther. Pat. 5(5): 459–468, 1995.
Eppley BL et al,. "Bioactivation of Free–Fat Transfers: A Potential New Approach to Improving Graft Survival," *Plastic and Reconstructive Surgery*, 90 (6), 1002–1030 (Dec., 1992).
Katagiri et al., "Overexpression of Catalytic Subunit p110α of Phosphatidylinositol 3–Kinase Increases Glucose Transport Activity with Translocation of Glucose Transporters in 3T3–L1 Adipocytes," *J. Biol. Chem.*, 271 (29), 16987–16990 (Jul. 19, 1996).
Setoguchi et al., "Stimulation of Erythropoiesis by In Vivo Gene Therapy: Physiologic Consequences of Transfer of the Human Erythropoietin Gene to Experimental Animals Using an Adenovirus Vector," *Blood*, 84 (9), 2946–2953 (Nov. 1, 1994.
Yamamoto et al., "Human VEGF gene transfer in vascular prosthesis," *Supplement to Circulation*, 94 (8), p. I–637, Abstract 3721 (Oct. 15, 1996).
Barinaga, "Obese' Protein Slims Mice", *Science*, 269, 475–476 (1995).

Behringer et al., "Dwarf Mice Produced by Genetic Ablation of Growth Hormone–Expressing Cells", *Genes &Development*, 2, 453–461 (1988).
Bernstein et al., "Genetic Ablation in Transgenic Mice", *Mol. Biol. Med.*, 6, 523–530 (1989).
Bovsun "Fat Drug no Prescription for Svelte Couch Potatoes", *Biotechnology Newswatch*, 1, 3, 4 (Aug. 7, 1995).
Brooks et al., Requirement of Vascular Integrin $\alpha_v\beta_3$ for Angiogenesis, *Science*, 264, 569–571 (1994).
Campfield et al., "Recombinant Mouse OB Protein: Evidence for a Peripheral Signal Linking Adiposity and Central Neural Networks", *Science*, 269, 546–549 (1995).
Clayman et al., "Transduction of Normal and Malignant Oral Epithelium by an Adenovirus Vector: The Effect of Dose and Treatment Time on Transduction Efficiency and Tissue Penetration", *Cancer Gene Therapy*, 2, 105–111 (1995).
E.S., "Gene Implants for Vessel–Sprouting Factor May Prevent Leg Amputation", *Biotechnology Newswatch*, 1,8 (Aug. 15, 1996).
Flier et al., "Severely Impaired Adipsin Expression in Genetic and Acquired Obesity", *Science*, 237 405–408 (1987).
Graves et al., "Identification of a Potent Adipocyte–Specific Enhancer: Involvement of an NF–1–like Factor", *Genes & Development*, 5; 428–437 (1990).
Halaas et al., "Weight–Reducing Effects of the Plasma protein Encoded by the *obese*Gene", Science, 269, 543–546 (1995).
Mühlhauser et al., $VEGF_{165}$ Expressed By a Replication–Deficient, Recombinant Adenovirus Vector Induces Angiogenesis In Vivo, *Circ. Res.*, 77, 1077–1086 (1995).
Palmiter et al., "Cell Lineage Ablation in Transgenic Mice by Cell–Specific Expression of a Toxin Gene", *Cell*, 50, 435–443 (1987).
Pelleymounter et al., "Effects of the obse Gene Product on Body Weight Regulation in ob/ob Mice", *Science*, 269, 540–543 (1995).

(List continued on next page.)

*Primary Examiner*—Jasemine C. Chambers
*Assistant Examiner*—Scott D. Priebe
*Attorney, Agent, or Firm*—Leydig, Voit & Mayer, Ltd.

[57] ABSTRACT

The present invention provides for in vivo gene transfer to adipocytes mediated by adenovirus and, in particular, the in vivo transfer of toxic genes as a means of reducing adiposity, as well as the transfer of genes encoding angiogenic substances to induce new blood vessel growth. The present invention also provides for the in vivo gene transfer to adipocytes to supply a source of proteins to be used in the local milieu of the adipocyte tissue or to be secreted and used systemically. Further, the present invention provides for the transfer of the adipocytes to other sites within a host, following adenoviral-mediated transfer of genes to the adipocytes in vivo, to allow for the exploitation of the modified adipocytes as a transferable means for the production of protein.

10 Claims, 5 Drawing Sheets

OTHER PUBLICATIONS

Ross et al., "A Fat–Specific Enhancer is the Primary Determinant of Gene Expression for Adipocyte P2 in vivo", *Pro. Natl. Acad. Sci*, 87, 9590–9594 (1990).

Ross et al., "Hibernoma Formation in Transgenic Mice and Isolation of a Brown Adipocyte Cell Line Expressing the Uncoupling Protein Gene", *Proc. Natl. Acad. Sci.*, 89, 7561–7565 (1992).

Ross et al., "Targeted Expression of a Toxin Gene to Adipose Tissue: Transgenic Mice Resistant to Obesity", *Genes &Development*, 7, 1319–1324 (1993).

Setoguchi et al., "Ex Vivo and In Vivo Gene Transfer to The Skin Using Replication–Deficient Recombinant Adenovirus Vectors", *The Journal of Investigative Dermatology*, 102, 415–421 (1994).

Shaffer, "Battle of the Bulge Enters Labs as Firms Seek Magic Bullet for Fat", *Biotechnology Newswatch*, 12, 13 (Apr. 1, 1996).

Spiegelman et al., Regulation of Adipocyte Gene Expression in Differentiation and Syndromes of Obesity/Diabetes, *The Journal of Biological Chemistry*, 268, 6823–6826 (1993).

Stone, "Rockefeller Strikes Fat Deal with Amgen-"*Science*268, 631 (1995).

ADENOVIRAL-MEDIATED GENE TRANSFER TO ADIPOCYTES

TECHNICAL FIELD OF THE INVENTION

The present invention relates to in vivo gene transfer to adipocytes mediated by adenovirus. The present invention also relates to vectors useful for the adenoviral-mediated transfer of genes to adipocytes.

BACKGROUND OF THE INVENTION

Gene therapy entails the use of genetic information as the pharmacologic agent. While originally conceived as a means of treating hereditary disease, gene therapy is now recognized as a powerful tool for delivering therapeutic mRNA or proteins for local and/or systemic use (see, e.g., Friedmann, *Science*, 244, 1275–1281 (1989); Miller, *Nature*, 357, 455–460 (1992)). Generally, there are two approaches to gene therapy: ex vivo and in vivo. In the ex vivo approach, cells removed from a host are genetically modified in vitro before being returned to the host (see, e.g., U.S. Pat. No. 5,399,346 (Anderson et al.)). In the in vivo approach, the genetic information itself is transferred directly to the host, without employing any cells as a vehicle for transfer.

Both approaches have been employed to transfer a so-called "therapeutic" gene to a host. Broadly considered, a therapeutic gene is a gene that corrects or compensates for an underlying protein deficit or, alternately, a gene that is capable of regulating another gene, or counteracting the negative effects of its encoded product, in a particular disease state, condition, disorder or syndrome. For instance, the ex vivo approach has been used for the modification of T lymphocytes in the treatment of adenosine deaminase deficiency, modification of hepatocytes in the treatment of familial hypercholesterolemia, and modification of tumor-infiltrating lymphocytes in the treatment of neoplastic disease (reviewed in Setoguchi et al., *J. Investig. Dermatol.*, 102, 415–421 (1994)). The in vivo approach has been used, among others, for the treatment of cystic fibrosis and neoplastic disease (Setoguchi et al., supra). For the majority of these applications, the coding sequence of the therapeutic gene to be expressed has been placed under the control of an alternative promoter (in particular, a constitutive or inducible promoter), generating a recombinant therapeutic gene.

The predominant approach to gene therapy has employed the retrovirus as a vehicle for gene transfer. However, retroviruses have a number of drawbacks which severely limit their application, particularly in vivo (Mastrangeli et al., *J. Clin. Invest.*, 91, 225–34 (1993); (Burns et al., *Proc. Natl. Acad. Sci.*, 90, 8033–37 (1993)). Consequently, many researchers have turned to the adenovirus as a vector for gene therapy (Horwitz, In: *Virology*, 2nd Ed., Fields et al., eds., (NY: Raven Press, 1990) 1679–1721; Berkner, K. L., *BioTechniques*, 6, 606–629 (1988); Ginsberg (ed.) *The Adenoviruses* (NY: Plenum Press, 1984); Horwitz, supra; Rosenfeld et al., *Science*, 252, 431–434 (1991); Rosenfeld et al., *Cell*, 68, 143–155 (1992); Quantin et al., *Proc. Natl. Acad. Sci.*, 89, 2581–2584 (1992); Crystal et al., *Nucleic Acids Res.*, 21, 1607–12 (1993)). Replication-deficient, recombinant adenovirus vectors are highly efficient at transferring genes in vitro and in vivo, and currently are used in a wide variety of applications (see, e.g., Rosenfeld et al. (1991), supra; Rosenfeld et al. (1992), supra; Crystal et al., *Nat. Genet.*, 8, 42–51 (1994); Lemarchand et al., *Circ. Res.*, 72, 1132–1138 (1993); Guzman et al., *Circ. Res.*, 73, 1202–1207 (1993); Bajocchi et al., *Nat. Genet.*, 3, 229–234 (1993); Mastrangeli et al., supra).

Adenoviruses exist as non-enveloped double-stranded DNA viruses (Horwitz, supra). The adenovirus provides an efficient means for transferring biological materials to target cells (Otero et al., *Virology*, 160, 75–80 (1987); FitzGerald et al., *Cell*, 32, 607–617 (1983); Seth et al., *Mol. Cell Biol.*, 4, 1528–1533 (1984); Yoshimura, *Cell Struct. Funct.*, 10, 391–404 (1985); Defer et al., *J. Virol.*, 64, 3661–3673 (1990); Rosenfeld et al. (1991), supra; Curiel et al., *Proc. Natl. Acad. Sci.*, 88, 8850–8854 (1991); Rosenfeld et al. (1992), supra; Quantin et al., supra; Curiel et al., *Hum. Gene Therapy*, 3, 147–154 (1992)). The adenovirus enters cells by a receptormediated endocytosis pathway. In the initial virus-receptor interaction, the adenovirus binds specific receptors present on the cell surface via fibers on its outer surface (Ginsberg, supra; Horwitz, supra; Seth et al., In: *Virus Attachment and Entry into Cells*, Colwell et al., eds., (DC: American Society for Microbiology, 1986) 191–195). Following attachment, the receptors with bound adenovirus cluster in coated pits, and the virus is internalized within a clathrin-coated vesicle and, subsequently, into an endosomal vesicle, termed an endosome, or receptosome (FitzGerald et al., supra). The adenovirus ultimately is translocated to the nucleus, where it directs the synthesis of nascent nucleic acids (FitzGerald et al., supra; Seth et al. (1984), supra; Seth et al. (1986) supra; Seth et al., *J. Virol.*, 51, 650–655 (1984a); Seth et al., *J. Biol. Chem.*, 259, 14350–14353 (1984b); Seth et al., *J. Biol. Chem.*, 260, 9598–9602 (1985); Seth et al., *J. Biol. Chem.*, 260, 14431–14434 (1985); Blumenthal et al., *Biochemistry*, 25, 2231–2237 (1986); Seth et al., *J. Virol.*, 61, 883–888 (1987)).

The ability of the adenovirus to easily enter cells has been seized upon as a means of transporting macromolecules into cells (Otero et al., supra; FitzGerald et al., supra; Seth et al. (1984), supra; Yoshimura, supra; Defer et al., supra; Rosenfeld et al. (1991), supra; Curiel et al. (1991), supra; Rosenfeld et al. (1992), supra; Quantin et al., supra; Curiel et al. (1992), supra). There are two means by which such transfer has been effected. First, the adenovirus has been employed to transfer non-viral macromolecules packaged within the adenovirus either in place of, or in addition to, normal adenoviral components (Rosenfeld et al. (1991), supra; Rosenfeld et al. (1992), supra; Quantin et al., supra; Berkner, supra). Second, the adenovirus has been employed to mediate the transfer of non-viral macromolecules either linked to the surface of the adenovirus (e.g., by means of conjugation of the nucleic acid through a polylysine residue to an antibody to adenoviral capsid protein (Curiel et al. (1992), supra)) or in a "bystander" process where the macromolecule is cointernalized and taken along as cargo in the adenoviral receptor-endosome complex (Otero et al., supra; FitzGerald et al., supra; Seth et al. (1984), supra; Yoshimura, supra; Otero et al., supra; Defer et al., supra). Such a bystander process has been employed to enhance the transfer of a variety of non-viral macromolecules including plasmid DNA linked to ligands (Curiel et al. (1991), supra; Curiel et al. (1992), supra; Cotten et al., *Proc. Natl. Acad. Sci.*, 89, 6094–098 (1992)); Rosenfeld et al. (1992), supra; Quantin et al., supra; Cotten et al., *J. Viroloqy*, 67, 3777–3785 (1993); Wagner et al., *Proc. Natl. Acad. Sci.*, 78, 144–145 (1981)), and plasmid DNA unmodified by nonspecific linkers or by linker-ligand complexes (Yoshimura et al., *J. Biolog. Chem.*, 268, 2300–303 (1993); PCT Application WO 95/21259 (Seth et al.)).

Recently, Setoguchi et al. (Setoguchi et al., supra) disclose adenoviral-mediated gene transfer to adipocytes in vivo of a replication-deficient recombinant adenoviral vector carrying the coding sequence of the β-galactosidase reporter gene under the control of the Rous sarcoma virus long terminal repeat as a promoter. Similarly, Clayman et al. (Clayman et al., *Cancer Gene Therapy*, 2, 105–111 (1995)) disclose that submucosal injection in mice of a recombinant adenoviral vector carrying a β-galactosidase reporter gene produces scattered staining of adipocytes along the needle track.

Other investigators working with vectors and means of delivery other than adenovirus have transferred genes other than reporter genes to adipocytes in vivo. Specifically, Ross et al. (Ross et al., *Genes Devel.*, 1318–1324 (1993)) disclose the reduction of adiposity via gene transfer to adipose tissue of an attenuated diphtheria toxin A chain under the control of the adipocyte-specific adipocyte P2 (aP2) promoter. Yamaizumi et al. (Yamaizumi et al., *Cell*, 15, 245–50 (1978)) disclose cell killing through the introduction of diphtheria toxin fragment A, and Gregory et al. (Gregory et al., PCT Application WO 95/11984) disclose means of inducing cell death, such as with use of the conditional suicide gene thymidine kinase. Similarly, Graves et al. (Graves et al., *Genes & Development*, 5, 428–37 (1991)) and Ross et al. (Ross et al., *Proc. Natl. Acad. Sci.*, 89, 7561–65 (1992); Ross et al., *Proc. Natl. Acad. Sci.*, 87, 9590–94 (1990)) each disclose an adipocyte-specific enhancer located in the 5'-regulatory region of the aP2 gene.

Other references similarly disclose methods for deleting specific cell lineages by cell-specific expression of a toxin gene (Palmiter et al., *Cell*, 50, 435–43 (1987); Bernstein et al., *Mol. Biol. Med.*, 6, 523–30 (1989); Behringer et al., *Genes & Development*, 2, 453–61 (1988); Hughes et al., PCT Application WO 92/09616)). The method employed typically calls for microinjecting into fertilized eggs a chimeric gene in which a cell-specific enhancer/promoter is used to drive the expression of a toxic gene product. In a modification of this approach, Hughes et al. (Hughes et al., supra) disclose reduction in the amount of fatty tissues of a host due to introduction of a vector encoding the chicken c-ski protein, which induces myogenic differentiation.

References not involving adenovirus as a means of gene transfer suggest further ways in which adipocytes can be modified in vivo to achieve specific therapeutic aims. Specifically, Spiegelman et al. (Spiegelman et al., *J. Biol. Chem.*, 268(10), 6823–26 (1993)) review the regulation of adipocyte gene expression and suggest "influencing metabolism by controlling adipogenic gene expression" and "[interfering] with adipogenesis and systemic metabolism by targeting these key regulators" associated with cell differentiation or obesity. Graves et al. (Graves et al., supra) suggest "the relationship between obesity and diabetes in several obese/diabetic mouse models . . . could be probed by directly suppressing adipose cell formation and/or lipid accumulation through the delivery of toxins or various receptors affecting lipid accumulation". Ross et al. (Ross et al. (1990), supra) disclose the production of transgenic mice containing the adipocyte-specific aP2 gene regulatory region linked to the coding sequence of a reporter gene as a means of monitoring tissue-specific expression and suggest "adipose-directed expression of exogenous genes may be an effective method to alter fat storage and thus directly manipulate the fatness of transgenic animals". Ross et al. (Ross et al. (1992), supra) further disclose the production of transgenic mice containing the adipocyte-specific aP2 gene regulatory region linked to the simian virus 40 (SV40) transforming genes as a means of directing expression of linked exogenous genes, such as oncogenes, to adipose tissue.

Other references also are relevant to adipocyte modification. Specifically, U.S. Pat. No. 5,268,295 (Serrero) relates to a mammalian adipocyte-specific polypeptide, termed p154, which is expressed in high quantities in adipogenic cell lines after differentiation. The '295 patent discloses the murine and human p154 polypeptide, as well as the DNA and RNA molecules coding therefor, methods for its preparation, and antibodies specific for the polypeptide. Flier et al. (Flier et al., *Science*, 237, 405–8 (1987)) disclose that expression of an adipsin gene and, correspondingly, circulating levels of the serine protease homolog are decreased in obesity. More recently, researchers have demonstrated that the protein product (Ob) of the mouse obese gene causes weight loss, and maintenance of the weight loss, when injected into animals (e.g., reviewed in Barinaga, *Science*, 269, 475–76 (1995)).

Accordingly, there is a need for an improved means of modifying adipocytes by transferring genes in vivo. It is an object of the present invention to provide such means, as well as vectors for effectuating such means. These and other objects and advantages of the present invention, as well as additional inventive features, will be apparent from the description of the invention provided herein.

BRIEF SUMMARY OF THE INVENTION

The present invention provides methods and vectors for adenoviral-mediated gene transfer to adipocytes, as a means of modifying adipocytes in vivo. The present invention also provides for the in vivo transfer of genes to adipocytes to provide a source of proteins to be used in the local milieu of the adipocyte tissue or to be secreted and used systemically. In particular, the present invention provides for the transfer of toxic genes to adipocytes in vivo as a means of reducing adiposity, and the transfer of genes encoding angiogenic substances to induce neovascularization. Furthermore, the present invention provides for the transfer of the modified adipocytes to other sites within a host, following adenoviral-mediated transfer of genes to the adipocytes in vivo, to allow for the exploitation of the modified adipocytes as a transferable means for the production of protein.

DETAILED DESCRIPTION OF THE INVENTION

Figure 1:
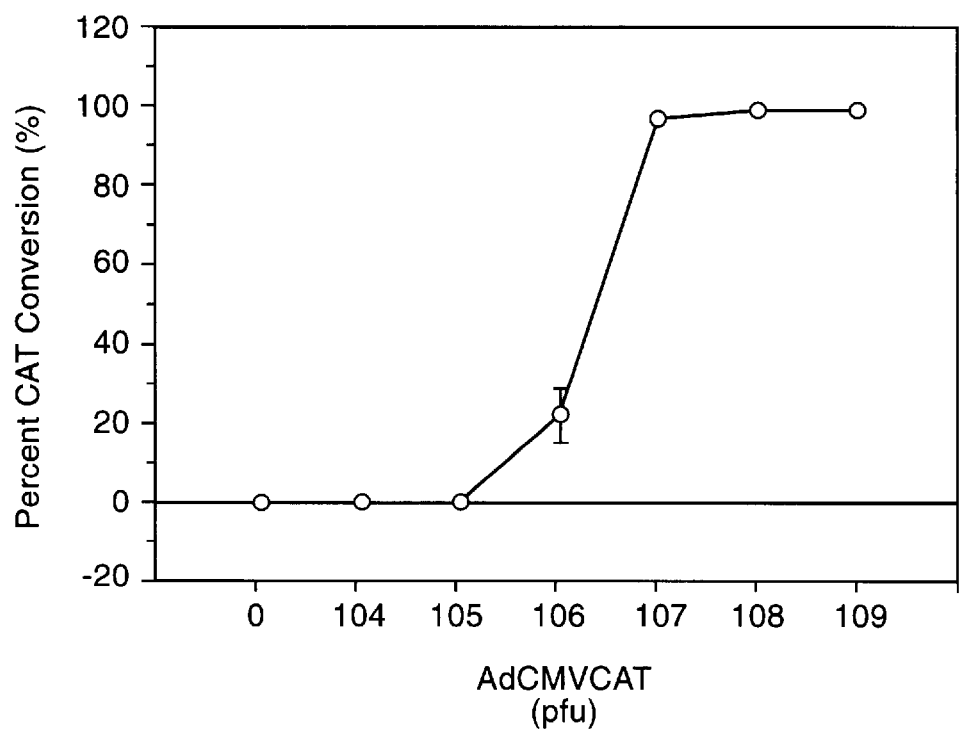
FIG. 1 is a graph of dose of AdCMVCAT (total pfu) delivered to rat retroperitoneal adipose tissue versus chloramphenicol acetyl transferase (CAT) conversion (% conversion).

The present invention provides a method of modifying an adipocyte in vivo which comprises contacting the adipocyte with an adenoviral vector comprising a promoter and, operably linked thereto, a nucleic acid sequence encoding a therapeutic protein or therapeutic mRNA, i.e., a protein or mRNA capable of exerting a therapeutic effect. Desirably the contacting is done under conditions such that entry of the adenoviral vector into the adipocyte is effected, the nucleic acid sequence is expressed, and the therapeutic protein or mRNA effect is thereby produced.

While any suitable adenoviral vector can be utilized in the method of the invention, the present invention preferably is carried out using the following vectors which also are provided by the invention. For instance, the method can be carried out using an adenoviral vector comprising an adipocyte-specific promoter and, operably linked thereto, a nucleic acid sequence encoding a therapeutic protein or therapeutic mRNA. In particular, the method can be carried out using an adenoviral vector comprising a constitutive promoter (optimally a CMV promoter) and, operably linked thereto, a nucleic acid sequence encoding a protein selected from the group consisting of a secreted protein which acts systemically and a protein which acts upon or in the vicinity of an adipocyte. The method also can be carried out using an adenoviral vector comprising a constitutive promoter (optimally a CMV promoter) and, operably linked thereto, a nucleic acid sequence encoding a protein selected from the group consisting of a toxin (especially diphtheria toxin A), an angiogenic growth factor (especially a vascular endothelial cell growth factor (VEGF or $VEGF_{165}$)), an adipsin (especially an adipsin which is a serine protease homolog), and a protein product of the obese gene, namely an Ob protein or leptin (especially an Ob protein from mouse or human). The present invention further provides host cells comprising the vectors of the present invention.

To optimize the ability of the adenovirus to enter the cell by the method of the invention, preferably the method is carried out in the absence of neutralizing antibodies directed against the particular adenovirus being introduced intracellularly. In the absence of such antibodies, there is no possibility of the adenovirus being bound by the antibody, and thus impeded from binding to and/or entering the cell. It is well within the ordinary skill of one in the art to test for the presence of neutralizing antibodies. In the event the presence of such neutralizing antibodies are an obstacle to the intracellular delivery of an adenovirus, another adenoviral vector, e.g., another serotype adenoviral vector (Crompton et al., *J. Gen. Virol.*, 75, 133–139 (1994)), or another adenovirus vector lacking the epitope against which the antibody is directed, can be employed.

Definitions

A "therapeutic gene" comprises a promoter and a nucleic acid sequence encoding a therapeutic protein or a therapeutic MRNA. Such as therapeutic gene can be subcloned into a vector according to the present invention, such that, upon introduction into a host cell, it will be is accompanied by a discernible change in the intracellular environment (e.g., by an increased level of deoxyribonucleic acid (DNA), ribonucleic acid (RNA), peptide or protein, or by an altered rate of production or degradation thereof), as further described herein to provide a therapeutic benefit. A "gene product" is either an as yet untranslated RNA molecule transcribed from a given nucleic acid sequence (e.g., mRNA or antisense RNA) or the polypeptide chain (i.e., protein or peptide) translated from the mRNA molecule transcribed from the aforesaid nucleic acid sequence. A nucleic acid sequence or gene is "recombinant" if the sequence of bases along the molecule has been altered from the sequence in which the nucleic acid sequence or gene is typically found in nature, or if the sequence of bases is not typically found in nature. According to this invention, a therapeutic gene can be wholly or partially synthetically made, can comprise genomic or complementary DNA (cDNA) sequences, and can be provided in the form of either DNA or RNA.

A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs (kb), even from a position downstream of a transcribed region. According to the invention, a nucleic acid sequence encoding a therapeutic protein or therapeutic mRNA is "operably linked" to a promoter (e.g., when both the nucleic acid sequence and the promoter constitute a therapeutic gene) when the promoter is capable of directing transcription of that nucleic acid sequence.

Vector

Any suitable adenoviral vector can be utilized in the present inventive method. A "vector" is a molecule (e.g., a virus such as adenovirus) that serves to transfer coding information to a host cell. Thus, the adenoviral vector utilized in accordance with the present inventive method can encompass any adenoviral vector that is appropriate for the introduction of nucleic acids into eukaryotic cells and is capable of functioning as a vector as that term is understood by those of ordinary skill in the art. The adenoviral vector in the context of the present invention contains one or more heterologous and/or recombinant sequences, e.g., a therapeutic gene comprising a promoter and a nucleic acid sequence encoding a therapeutic protein or therapeutic mRNA, possibly one or more enhancers or silencers, and the like. A sequence is "heterologous" if it is present in a different genome from which it is typically found.

The adenovirus can be any serotype of adenovirus (see, e.g., *Fields Virology*, Fields et al. (Eds.), 3rd Ed., (NY: Raven Press, 1996) 2111–2171)) and, preferably, is a serotype that can transduce and/or infect a human cell. Desirably, the adenovirus comprises a complete adenoviral virus particle (i.e., a virion) consisting of a core of nucleic acid and a protein capsid, or comprises a protein capsid to which DNA comprising a therapeutic gene is appended, or comprises a naked adenoviral genome, or is any other manifestation of adenovirus as described in the art and which can be used to transfer a therapeutic gene. In the context of the present invention, any suitable adenoviral genome can serve as, or be a part of, the adenoviral vector. Preferred adenoviral genomes include those derived from Ad5 and Ad2, which are easily isolated from infected cells, are commercially available (e.g., from Sigma Chemical Co., St. Louis, Mo.), or are generally available from those skilled in the art who routinely maintain these viral stocks.

For the purpose of this invention, the adenovirus employed for transfer of a therapeutic gene can be wildtype (i.e., replication-competent). However, it is not necessary that the genome of the employed adenovirus be intact. In fact, to prevent the virus from usurping host cell functions and ultimately destroying the cell, the adenovirus can be inactivated prior to its use, for instance, by UV irradiation. Alternately, the adenovirus can comprise genetic material with at least one modification therein, which can render the virus replication-deficient. Also, the adenovirus can consist of a therapeutic gene linked to an adenoviral capsid, and thus may not possess an adenoviral genome. Moreover, the virus can be coupled to a DNA-polylysine complex containing a ligand (e.g., transferrin) for mammalian cells such as has been described in the art (see, e.g., Wagner et al., supra).

The modification to the adenoviral genome can include, but is not limited to, addition of a DNA segment, rearrangement of a DNA segment, deletion of a DNA segment, replacement of a DNA segment, methylation of unmethylated DNA, demethylation of methylated DNA, and introduction of a DNA lesion. For the purpose of this invention, a DNA segment can be as small as one nucleotide and as large as 36 kilobase pairs (kb) (i.e., the size of the adenoviral genome) or, alternately, can equal the maximum amount which can be packaged into an adenoviral virion (i.e., about 38 kb).

Such modifications to the adenoviral genome can render the adenovirus replication-deficient. Preferably, however, the modification does not alter the ability of the adenovirus to bind to a suitable cell surface receptor. Preferred modifications to the adenoviral genome include modifications in the E1, E2, E3, and/or E4 regions.

The vector utilized in the context of the present invention can comprise sequences so as to constitute any type of suitable vector. For example, the vector can comprise a mammalian expression vector, a vector in which the subcloned coding sequence of the therapeutic gene is under the control of its own cis-acting regulatory elements, or a vector designed to facilitate gene integration or gene replacement in host cells. Preferably the vector comprises an expression vector appropriate for expression of a therapeutic gene in a mammalian (optimally, human) cell.

The vector according to the invention also can comprise a vector other than an adenoviral vector (e.g., a plasmid, phage, liposomal or other viral vector), or a ligation of adenovirus sequences with other vector sequences. However, while these other vectors can be employed, for instance, in the construction of adenoviral vectors, preferably an adenoviral vector (i.e., as compared to a phage, plasmid or other vector) is employed to transfer genes to adipocytes in vivo.

Vector identification and/or selection can be accomplished using a variety of approaches known to those skilled in the art. For instance, vectors containing particular nucleic acid sequences can be identified by hybridization, the presence or absence of so-called "marker" gene functions encoded by marker genes present on the vectors, and/or the expression of particular sequences. In the first approach, the presence of a particular sequence in a vector can be detected by hybridization (e.g., by DNA-DNA hybridization) using probes comprising sequences that are homologous to the relevant sequence. In the second approach, the recombinant vector/host system can be identified and selected based upon the presence or absence of certain marker gene functions such as resistance to antibiotics, thymidine kinase activity, and the like, caused by particular genes encoding these functions present on the vector. In the third approach, vectors can be identified by assaying for a particular gene product encoded by the vector. Such assays can be based on the physical, immunological, or functional properties of the gene product.

Therapeutic Gene

The vector used in the context of the present invention can comprise one or more therapeutic genes. Any suitable therapeutic gene can be employed according to the present invention, so long as the therapeutic gene is capable of being transcribed in a cell in which the vector has been internalized.

The therapeutic gene being transferred can comprise DNA which can be as small as one repeat unit (e.g., a nucleotide) and as large as reasonably can be isolated, synthesized, or transferred to a host cell using the methods of the present invention and considering the packaging constraints of viral vectors. The therapeutic gene comprises non-coding sequences (such as a promoter) as well as a nucleic acid sequence encoding a therapeutic protein or therapeutic mRNA. The "nucleic acid sequence" of the therapeutic gene preferably comprises sense or antisense sequences, including ribozymes, or catalytic RNA species such as described in the art (Hampel et al., *Nucleic Acids Research*, 18, 299–304 (1990); Cech et al., *Annual Rev. Biochem.*, 55, 599–629 (1986)), as well as engineered sequences, or sequences which are not normally present in vivo.

The nucleic acid sequence of the therapeutic gene can be in any orientation in the vector. The therapeutic gene nucleic acid sequence can be placed under the control of (i.e., "operably linked to") 5' and/or 3' regulatory sequences (e.g., promoters) which typically either do or do not control the coding sequence (e.g., the sense or antisense mRNA sequence) in its native form. In particular, any promoter can be substituted for the native promoter of the nucleic acid sequence to generate a recombinant therapeutic gene. Furthermore, the therapeutic gene can contain lesions including, but not limited to, a missing base or altered base (e.g., an alkylated base), a cyclobutyl dimer, strand breaks, and cross-linking of nucleic acid strands.

The therapeutic gene typically will exert its effect at the level of RNA or protein for the purpose of treating a disease or condition. The therapeutic gene can exert its effect at the level of RNA, for instance, by comprising a nucleic acid sequence that encodes a therapeutic mRNA such as an antisense message or ribozyme or a protein which affects splicing or 3' processing (e.g., polyadenylation). Alternately, the nucleic acid sequence of the therapeutic gene can encode a therapeutic protein which acts by affecting the level of expression of another gene within the cell (i.e., where gene expression is broadly considered to include all steps from initiation of transcription through production of a processed protein), including, among other things, by mediating an altered rate of mRNA accumulation, an alteration of MRNA transport, and/or a change in post-transcriptional regulation.

Also, a protein encoded by the nucleic acid sequence of a transferred therapeutic gene can be employed in the treatment of an inherited disease, such as, e.g., the cystic fibrosis transmembrane conductance regulator cDNA for the treatment of cystic fibrosis. The protein encoded by the therapeutic gene nucleic acid sequence can exert its therapeutic effect by resulting in cell killing. For instance, expression of the gene itself can lead to cell killing, as with the expression of the diphtheria toxin A gene, or the expression of the gene can render cells selectively sensitive to the killing action of certain drugs, e.g., expression of the HSV thymidine kinase gene renders cells sensitive to antiviral compounds including acyclovir, gancyclovir, and FIAU (1-(2-deoxy-2-fluoro-β-D-arabinofuranosil)-5-iodouracil). This is of particular value in the reduction of adiposity according to the invention, wherein adipocytes are killed by the transferred gene. Similarly, expression of the gene can result in new blood vessel growth, as where the therapeutic gene nucleic acid sequence encodes an angiogenic substance.

Accordingly, the therapeutic gene nucleic acid sequence preferably encodes a protein selected from the group consisting of a secreted protein which acts systemically and a protein which acts upon or in the vicinity of an adipocyte.

More preferably, the therapeutic gene nucleic acid sequence encodes a protein selected from the group consisting of a toxin, especially diphtheria toxin A or a similar gene encoding a toxin (Yamaizumi et al., supra; Ross et al. (1993), supra; Palmiter et al., supra; Bernstein et al., supra; Behringer et al., supra; Hughes et al., supra), p154 polypeptide, especially the p154 polypeptide obtained from a human or mouse gene (Serrero, supra), an adipsin, especially an adipsin which is a serine protease homolog (Flier et al., supra), an Ob protein such as a leptin, especially an Ob protein obtained from a human or mouse obesity gene (Zhang et al., *Nature*, 372, 425 (1994); Murakami et al., *Biochem. Biophys. Res. Commun.*, 209, 944 (1995); Considine et al., *J. Clin. Invest.*, 95, 2986 (1995)) or OB polypeptides such as have been described in the art (see, e.g., Great Britain Application 2,292,382), and an angiogenic substance such as a growth factor, especially VEGF, particularly VEGF$_{165}$ (Muhlhauser et al., *J. Cell Biochem.*, 18A, DZ315 (1994)), or other angiogenic growth factors such as have been described in the art (see, e.g., Cid et al., supra) and are further described herein.

Promoter

Any promoter (i.e., whether isolated from nature or produced by recombinant DNA or synthetic techniques) can be used in connection with the present invention to provide for gene transcription. The promoter preferably is capable of directing transcription in a eukaryotic (desirably mammalian) cell. The functioning of the promoter can be altered by the presence of one or more enhancers and/or silencers present on the vector.

The DNA sequences appropriate for expression in eukaryotic cells (i.e., "eukaryotic promoters") differ from those appropriate for expression in prokaryotic cells. Generally, eukaryotic promoters and accompanying genetic signals are not recognized in or do not function in prokaryotic systems, and prokaryotic promoters are not recognized in or do not function in eukaryotic cells.

A comparison of promoter sequences that function in eukaryotes has revealed conserved sequence elements. Generally, eukaryotic promoters transcribed by RNA polymerase II are typified by a "TATA box" centered around position –25 which appears to be essential for accurately positioning the start of transcription. The TATA box directs RNA polymerase to begin transcribing approximately 30 base pairs (bp) downstream in mammalian systems. The TATA box functions in conjunction with at least two other upstream sequences located about 40 bp and 110 bp upstream of the start of transcription. Typically, a so-called "CCAAT box" serves as one of the two upstream sequences, and the other often is a GC-rich segment (e.g., a "GC box" comprised, for instance, of the sequence GGGCGG, or the sequences GCCACACCC and ATGCAAAT). The CCAAT homology can reside on different strands of the DNA. The upstream promoter element also can be a specialized signal such as those which have been described in the art and which appear to characterize a certain subset of genes.

To initiate transcription, the TATA box and the upstream sequences are each recognized by regulatory proteins which bind to these sites, and activate transcription by enabling RNA polymerase II to bind the DNA segment and properly initiate transcription. Whereas base changes outside the TATA box and the upstream sequences have little effect on levels of transcription, base changes in either of these elements substantially lower transcription rates (e.g., Myers et al., *Science*, 229, 242–247 (1985); McKnight et al., *Science*, 217, 316–324 (1982)). The position and orientation of these elements relative to one another, and to the start site, are important for the efficient transcription of some, but not all, coding sequences. For instance, some promoters function well in the absence of any TATA box. Similarly, the necessity of these and other sequences for promoters recognized by RNA polymerase I or III, or other RNA polymerases, can differ.

Accordingly, promoter regions can vary in length and sequence and can further encompass one or more DNA-binding sites for sequence-specific DNA binding proteins and/or an enhancer or silencer. Enhancers and/or silencers can similarly be present on a vector outside of the promoter per se. The present invention preferentially employs within a therapeutic gene a constitutive promoter, in particular the cytomelagovirus (CMV) promoter, for regulating a coding sequence of interest. Such promoters, as well as mutations thereof, are known and have been described in the art (see, e.g., Boshart et al., *Cell*, 41, 521–530 (1985)). Other promoters, however, also can be employed, such as the Ad2 or Ad5 major late promoter and tripartite leader, the Rous sarcoma virus (RSV) long terminal repeat, and other constitutive promoters such as have been described in the literature. For instance, the herpes thymidine kinase promoter (Wagner et al., supra), the regulatory sequences of the metallothionine gene (Brinster et al., *Nature*, 296, 39–42 (1982)), promoter elements from yeast or other fungi such as the Gal 4 promoter, the alcohol dehydrogenase promoter, the phosphoglycerol kinase promoter, and the alkaline phosphatase promoter, can be employed. Similarly, promoters isolated from the genome of mammalian cells or from viruses that grow in these cells (e.g., adenovirus, SV40, herpes simplex virus, and the like) can be used.

Instead of being a constitutive promoter, the promoter can be a promoter which is up- and/or down-regulated in response to appropriate signals. For instance, an inducible promoter, such as the IL-8 promoter, which is responsive to TNF or another cytokine can be employed. Other examples of suitable inducible promoter systems include, but are hot limited to, the metallothionine inducible promoter system, the bacterial lacZYA expression system, the tetracycline expression system, and the T7 polymerase system. Further, promoters that are selectively activated at different developmental stages (e.g., globin genes are differentially transcribed in embryos and adults) can be employed.

In addition, a tissue-specific promoter, i.e., a promoter that is preferentially activated in a given tissue and results in expression of a gene product in the tissue where activated, particularly an adipocyte-specific promoter, can be used. Preferred adipocyte-specific promoters according to the invention include the aP2 gene regulatory region (e.g., Ross et al. (1990, 1992 and 1993) supra) and the p154 polypeptide gene regulatory region (Serrero, supra).

Gene Transfer

In the method of the present invention, one or more vectors are transferred to a host cell, which is preferably a eukaryotic host cell, optimally an adipocyte. The eukaryotic host cell can be present in vitro or in vivo, and, optimally, is present in vivo. According to the present invention, the "contacting" of cells with the vectors of the present invention can be by any means by which the vectors will be introduced into the cell. Such introduction can be by any suitable method. Preferably the adenoviral vectors will be introduced by means of infection or transduction, i.e., using the natural capability of the virus to enter cells and mediate uptake of bystander macromolecules (e.g., the capability of adenovirus to undergo receptor-mediated endocytosis). However, the vectors also can be introduced by any other suitable means, e.g., by transfection, calcium phosphate-mediated transformation, microinjection, electroporation, osmotic shock, and the like.

The method of the present invention can be effectively carried out using a wide variety of different types of adipocytes. The method can be employed with respect to various cells differing both in number of adenovirus receptors as well as in the affinity of the cell surface receptors for adenovirus. Accordingly, the types of cells to which gene delivery is contemplated in vitro or in vivo in the context of the present invention include avian cells, fish cells, and mammalian cells including but not limited to rodent, ape, chimpanzee, feline, canine, ungulate (such as ruminant or swine), and, more preferably, human cells.

The adenoviral vectors can be made into compositions appropriate for contacting cells with appropriate (e.g., pharmaceutically acceptable) excipients such as carriers, adjuvants, vehicles, or diluents. The means of making such a composition, and means of administration, have been described in the art (see, for instance, *Remington's Pharmaceutical Sciences*, 16th Ed., Mack, ed. (1980)). Where appropriate, the vectors can be formulated into preparations in solid, semisolid, liquid or gaseous forms such as tablets, capsules, powders, granules, ointments, solutions, suppositories, injections, inhalants, and aerosols, in the usual ways for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or. in appropriate association, as well as in combination, with other pharmaceutically active compounds. For example, in applying the methods of the present invention for delivery of a nucleic acid encoding a VEGF polypeptide to cells in need of angiogenic stimulation (e.g., in the enhancement of collateral circulation where there has been vascular occlusion or stenosis), such delivery can be employed in conjunction with other means of stimulating angiogenesis, such as, for example, treatment with other angiogenic growth factors, or use in combination with matrigel (a complex mixture of tumor basement membrane components and growth factors) (Mühlhauser et al., *Circ. Res.*, 77, 1077–86 (1995)).

Accordingly, the pharmaceutical composition of the present invention can be delivered via various routes and to various sites in an animal body to achieve a particular effect (see, e.g., Rosenfeld et al. (1991), supra; Rosenfeld et al., *Clin. Res.*, 39(2), 311A (1991a); Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

Accordingly, the present invention also provides a method of transferring a therapeutic gene to a host, which comprises administering the vector of the present invention, preferably as part of a composition, using any of the aforementioned routes of administration or alternative routes known to those skilled in the art and appropriate for a particular application. The "effective amount" of the composition is such as to produce the desired effect in a host which can be monitored using several end-points known to those skilled in the art. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer). One such particularized assay described in the examples herein includes the Western immunoassay for the detection of the protein encoded by a VEGF gene.

These methods described herein are by no means all-inclusive, and further methods to suit the specific application will be apparent to the ordinary skilled artisan. Moreover, the effective amount of the compositions can be further approximated through analogy to compounds known to exert the desired effect (e.g., compounds traditionally employed to stimulate angiogenesis can provide guidance in terms of the amount of a VEGF nucleic acid to be administered to a host).

Furthermore, the preferred amounts of each active agent included in the compositions according to the invention (e.g., per each cell to be contacted, preferably from about 1 to at least about 1000 adenoviral plaque forming units (PFU), more preferably from about 1 to at least about 100 adenoviral PFU, although any suitable amount can be utilized either above, i.e., greater than about 1000, or below, i.e., less than about 1, these preferred ranges) provide general guidance of the range of each component to be utilized by the practitioner upon optimizing the methods of the present invention for practice either in vitro or in vivo. Moreover, such ranges by no means preclude use of a higher or lower amount of a component, as might be warranted in a particular application. For instance, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of adenoviral receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Also, for these embodiments, when one or more different vectors (i.e., each encoding one or more different therapeutic genes) are employed in the methods described herein, the contacting of cells with the various components of the present invention can occur in any order or can occur simultaneously. Preferably the contacting will occur simultaneously. In a preferred embodiment, the component vectors of the present invention can be mixed together and preincubated prior to contacting the cell. When multiple vectors are to be administered, the cell is preferably contacted with the first vector less than about 6 weeks after, or less than about 6 weeks before, the cell is contacted with another vector. Even more preferably the cell is contacted with the first vector less than about 2 weeks after, or less than about 2 weeks before, the cell is contacted with another vector.

Adipocytes infected in vivo in accordance with the present invention can be transferred to another site within the host as a vehicle for the delivery of the protein encoded by the transferred gene to another anatomic locale, such a transfer can be effected by any suitable technique, such as those that are known in the art (see, e.g., Zhang et al., *Microsurgery*, 15, 269–73 (1994); Boyce et al. *Otolaryngol. Clin. North Am.*, 27, 39–68 (1994); Moscona et al., *Ann. Plast. Surg.*, 33, 500–6 (1994); Krabatsch et al., *J. Card. Surg.*, 10, 46–51 (1995)). The adipocytes so transferred need not be from the same host, or even the same species of host. Preferably, however, the adipocytes are transferred within the same host.

Other Considerations

With respect to the transfer and expression of therapeutic genes according to the present invention, the ordinary skilled artisan is aware that different genetic signals and processing events control levels of nucleic acids and proteins/peptides in a cell, such as, for instance, transcription, mRNA translation, and post-transcriptional processing. Transcription of DNA into RNA requires a functional promoter, as previously described. The amount of transcription is regulated by the efficiency with which RNA polymerase can recognize, initiate, and terminate transcription at specific signals. These steps, as well as elongation of the nascent mRNA and other steps, are all subject to being affected by various other components also present in the cell, e.g., by other proteins which can be part of the transcription process, by concentrations of ribonucleotides present in the cell, and the like.

Protein expression also is dependent on the level of RNA transcription which is regulated by DNA signals, and the levels of DNA template. Similarly, translation of mRNA requires, at the very least, an AUG initiation codon which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, *J. Molec. Biol.*, 196, 947–950 (1987)). Also, successful expression of a therapeutic gene in a cell can require post-translational modification of a resultant protein/peptide. Thus, production of a recombinant protein or peptide can be affected by the efficiency with which DNA (or PNA) is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production following recombination, preferably the vector employed for transfer of a therapeutic gene further comprises a polyadenylation site following the coding region of the therapeutic gene. Also, preferably all the proper transcription signals (and translation signals, where appropriate) will be correctly arranged on the recombinant vector such that the therapeutic gene will be properly expressed in the cells into which it is introduced. If desired, the vector can also incorporate splice sites (i.e., splice acceptor and splice donor sites) to facilitate mRNA production. Moreover, if the therapeutic gene being transferred encodes a protein which is a processed or secreted protein or, for instance, functions in an intracellular organelle such as mitochondria or endoplasmic reticulum, preferably the vector further contains the appropriate sequences for processing, secretion, intracellular localization, and the like.

With respect to promoters, coding sequences, therapeutic genes, marker genes, and the like, located on a vector according to the present invention, such elements are as previously described and can be present as part of a cassette, either independently or coupled. In the context of the present invention, a "cassette" is a particular base sequence that possesses functions which facilitate subcloning and recovery of nucleic acid sequences (e.g., one or more restriction sites) or expression (e.g., polyadenylation or splice sites) of particular nucleic acid sequences.

Illustrative Uses

The present invention provides methods and vectors for transferring genes to adipocytes in vivo and has particular utility with respect to diseases or conditions that can be treated directly by in vivo gene transfer to adipocytes. Because of the widespread effects of adipocytes on host metabolism, the present invention is preferably employed for the treatment of an energy storage disorder, such as a disorder selected from the group consisting of obesity, diabetes, increased body fat deposition, hyperglycemia, hyperinsulinemia, hypothermia, hypertension, hypercholesterolemia, hyperlipidemia, and the like.

The present inventive methods also have utility with respect to the treatment of other diseases or conditions. Specifically, according to the present invention, adenovirus can be employed to transfer genes to adipocytes in vivo, and, following establishment of at least a limited infection in adipocyte tissue, the infected adipocytes can be transferred to another site in the host, at which site the protein encoded by the transferred gene can exert its effect. Using adipocytes as a vehicle for the transfer of the gene in this fashion is advantageous, since adipocytes typically are non-immunogenic, unlike certain other tissue grafts which might be employed as a vehicle to transfer genes. Moreover, the approach ensures that the vascular supply to the region of the tissue graft remains undisturbed, unlike more invasive approaches that might be employed for treatment.

In particular, this method of the present invention can be employed to deliver proteins such as angiogenic substances or growth factors to areas of ischemia, such as the heart or muscle, or, more generally, in the treatment of ischemic disease. Angiogenesis is the process by which new blood vessels are formed from extant capillaries. Thus, the angiogenic process and the angiogenic factors which regulate the process are relevant to embryonic development, inflammation, and wound healing, and also contribute to pathologic conditions such as diabetic retinopathy, rheumatoid arthritis, cancer, and chronic inflammatory diseases (see, e.g., U.S. Pat. No. 5,318,957 (Cid et al.); Brooks et al., *Science*, 264, 569–571 (1994)). Accordingly, the present inventive approach can further be employed to deliver angiogenic growth factors to a host, or to particular regions of the host, to stimulate angiogenesis as a means to facilitate wound healing, as well as to treat cancer or inflammation (especially inflammation of blood vessels or systemic vasculitis). In particular, the approach can be employed in a biobypass method wherein instead of performing a more invasive procedure, such as a coronary bypass operation, a vector comprising an angiogenic gene is injected, and new blood vessels are induced to grow around the blocked region. Genes encoding the following angiogenic growth factors, and which have been described in the art (see, e.g., Cid et al., supra), can be used according to the present invention along with further angiogenic substances: vascular endothelial cell growth factor (VEGF), particularly $VEGF_{165}$, acidic fibroblast growth factor (aFGF), basic fibroblast growth factor (bFGF), transforming growth factor, alpha and beta tumor necrosis factor, platelet-derived growth factor, and angiogenin.

Furthermore, adipocytes in vivo can be employed as a site for the transfer of a gene encoding a protein which exerts its effects locally in the region of the adipocyte tissue or systemically, as for genes encoding secreted proteins which, following their production in adipocytes, diffuse into the bloodstream. Thus, the present inventive methods and vectors also can be used in the treatment of diseases or conditions not directly associated with adipocytes and/or metabolic processes affected thereby.

For instance, the method preferably can be employed to transfer genes that encode VEGF (particularly $VEGF_{165}$), aFGF and bFGF, as well as other angiogenic growth factors which can act locally to stimulate angiogenesis in the setting of tissue ischemia. Adenoviral vector transfer of genes encoding angiogenic substances can be employed to provide high concentrations of such substances in a regional fashion for a sustained period, thus inducing angiogenesis in the local milieu, yet minimizing the risk of chronic overinduction of angiogenesis in the target tissue, and promiscuous induction of angiogenesis in sensitive nondiseased organs, such as the retina or synovium, or in occult tumors (Folkman et al., *J. Biol. Chem.*, 267, 10931–34 (1992)). Similarly, the method preferably can be employed to transfer genes that encode 5-fluorouracil (5-FU) and as cis-platinum as well as other chemotherapeutic agents that can act locally to stimulate a cytopathic effect for the treatment of cancer cells.

For secreted proteins that act systemically, the present inventive methods can be employed using vectors which encode various therapeutic genes. For instance, the therapeutic gene can comprise, but is not limited to, the gene for α1-antitrypsin or adenosine deaminase for the treatment of inherited deficiency, factor VIII for hemophilia, other coagulation factors for bleeding disorders, erythropoietin for chronic renal failure and marrow suppressive disorders, proteins for enhancing the host defense response (e.g., antiviral proteins or immunomodulators), and antitumor agents (e.g., tumor suppressor proteins and interferons). Moreover, the present inventive methods and vectors can further be employed to deliver pharmacologics such as antihypertensives and anticoagulants, or receptor agonists or antagonists, using adipocytes infected in vivo as the means of producing these agents.

In regard to the use of the VEGF protein to induce therapeutic angiogenesis, several studies have demonstrated that the administration of VEGF protein in the setting of ischemia is capable of inducing the development of networks of new blood vessels in vivo. A single intraarterial bolus or repeat administration of VEGF induced increased vascularity and blood flow, and improved both hemodynamic and clinical function in rabbit hind limb models of ischemia (Ferrara et al., *Ann. N.Y. Acad. Sci.*, 752, 246–256 (1995); Takeshita et al., *Circulation*, 90, II228–II234 (1994); Takeshita et al., *J. Clin. Invest.*, 93, 662–670 (1994a); Bauters et al., *Am. J. Physiol.*, 267, H1263–H1271 (1994)). A similar model has been used to demonstrate a synergistic effect of VEGF and bFGF on angiogenesis in vivo (Asahara et al., *Circulation*, 92, II-365–II-371 (1995)). In a canine model of myocardial ischemia using an ameroid constrictor on the left circumflex coronary artery (LCx), daily administration of VEGF via an indwelling catheter in the distal LCx for 28 days resulted in an increase in collateral blood flow to ischemic myocardium and an increase in the density of intramyocardial distribution vessels (Banai et al., *Circulation*, 89, 2183–2189 (1994)). Also, in a porcine model of chronic ischemia using an ameroid constrictor, continuous administration of VEGF to the myocardium over 6 weeks resulted in myocardial angiogenesis as demonstrated by magnetic resonance imaging, showing a reduced ischemic zone, less contrast arrival delay, and improved ejection fraction and myocardial wall thickening (Pearlman et al., *Nature Med.*, 1, 1085–1089 (1995)).

Delivery of the VEGF gene (as well as other genes) using this approach is advantageous since gene transfer provides an equivalent of a "sustained-release capsule," providing high concentrations of the therapeutic protein for a sustained period. In comparison, the VEGF protein and certain other proteins have a very short biologic half-life (e.g., 6 minutes for VEGF) (Takeshita et al. (1994a), supra). While animal models of hind limb ischemia do show induction of angiogenesis with a single intraarterial bolus of the VEGF protein (Takeshita et al. (1994a), supra,) intramuscular administration for limb ischemia requires repetitive administration over several days (Takeshita et al. (1994), supra), as does intracoronary administration for myocardial ischemia (Banai et al., supra; Pearlman et al., supra). In comparison, the AdCMV.VEGF vector can provide sustained expression of the VEGF protein for at least 5 days. Also, gene transfer can be strategized to provide regional delivery of high concentration of VEGF to the ischemic limb or ischemic myocardium. In comparison, systemic administration of an angiogenic factor carries the theoretical risk of inducing inappropriate angiogenesis at sites of vascular derangement or at sites where angiogenesis might have major adverse consequences, such as the retina, the synovium and in occult tumors (Folkman et al., *J. Biol. Chem.*, 267, 10931–10934 (1992)). Finally, systemic administration of VEGF has been reported to cause hypotension in rats (Yang et al., *Circulation*, 92, I-713 (Abstract)(1995)). Clinical applications for which adenoviral-mediated delivery of VEGF or other genes (particularly genes encoding angiogenic substances) might be useful include non-bypassable ischemic heart disease or peripheral vascular disease, reinforcement of ischemic anastomoses, and acceleration of wound healing.

In comparison to the use of adenovirus for gene delivery to adipocytes in vivo, other gene transfer systems that presently are in clinical trials (e.g., retrovirus, adeno-associated virus, plasmid-liposome complexes, and the use of naked plasmid DNA)) (reviewed in Crystal et al., *Science*, 270, 404–410 (1995)) theoretically could be employed instead. While naked plasmids delivered to a proximal artery appear to provide sufficient VEGF to induce angiogenesis in the rabbit hind limb ischemia model (Takeshita et al., "Therapeutic Angiogenesis Following Arterial Gene Transfer of Vascular Endothelial Growth Factor in a Rabbit Model of Hind Limb Ischemia", *Proc. Natl. Acad. Sci.*, (in press) (1995)) and are being evaluated in a clinical trial (Isner, "Arterial Gene Transfer for Restenosis", Recombinant DNA Advisory Committee (RAC) Report No. 9508-118 (Office of Recombinant DNA Activities, NIH: Bethesda, Md. (1995)), expression from naked plasmids delivered in vivo is several orders of magnitude less than that observed using an adenovirus vector system (Crystal et al. (1995), supra; Nabel et al., *Cardiovasc. Res.*, 28, 445–455 (1994)). For in vivo gene transfer, retrovirus vectors are limited secondary to their sensitivity to inactivation in vivo and their requirement for target cell proliferation to transfer the new gene (Crystal et al., (1995), supra). Plasmid-liposome complexes are relatively inefficient for in vivo cardiovascular-related gene transfer (Crystal et al. (1995), supra; Nabel et al., supra). In contrast, adenoviral vectors have the aforementioned properties that make them ideal for the delivery of genes to adipose tissue as described herein and, particularly, for the delivery of VEGF-related genes for therapeutic angiogenesis. For instance, adenoviral vectors are effective at transferring genes to cardiovascular tissues, with high levels of expression of the gene for at least one week. This is particularly advantageous in view of the short half-life of the VEGF protein. Moreover, the self-limited nature of adenoviral-mediated gene expression means a decreased (and decreasing over time) risk of evoking too much angiogenesis in the target tissue. The new gene transferred by an adenoviral vector functions in an epichromosomal position, in contrast to adeno-associated virus and retrovirus vectors that integrate the exogenous gene into the chromosome of the target cell, and thus carry the risk of inappropriately delivering the angiogenic stimulus long after it is needed, and the risk of interference with the regulation/expression of a endogenous gene. Furthermore, adenovirus vectors achieve gene transfer to both dividing and non-dividing cells with high levels of efficiency, and produce localized and sustained levels of protein expression in a number of cardiovascular related sites, such as skeletal muscle, myocardium, vascular endothelium, and now, adipose tissue.

Additional uses and benefits of the invention will be apparent to one of ordinary skill in the art.

EXAMPLES

The following examples further illustrate the present invention and, of course, should not be construed as in any way limiting its scope.

Example 1

This example describes the construction of the adenoviral vectors employed in the experiments described further herein and described in Magovern et al., "Regional Angiogenesis induced in Non-Ischemic Tissue by an Adenovirus Vector expressing Vascular Endothelial Growth Factor" (submitted for publication).

Several replication-deficient, recombinant adenoviral vectors were employed to assess gene transfer to adipocytes in vivo. These vectors include Ad.RSVβgal, AdCMVCAT, and AdCMV.VEGF. Ad.RSVβgal is an E1$^-$E3$^-$ Ad5-based vector which contains the *Escherichia coli* β-galactosidase coding sequence under the control of the long terminal repeat of the Rous sarcoma virus as a promoter, and which follows the SV40 nuclear localization signal, as previously described (Setoguchi et al., supra). AdCMV.VEGF (i.e., AdCMV.VEGF$_{165}$) is a E1a$^-$, partial E1b$^-$, partial E3$^-$ adenoviral vector that contains an expression cassette in the E1 position containing the cytomegalovirus (CMV) immediate early promoter/enhancer driving the cDNA for the 165 amino acid form of human VEGF (i.e., VEGF$_{165}$, Mühlhauser et al., *Circ. Res.*, 77, 1077–1086 (1995)). AdCMV-CAT is similar to AdCMV.VEGF, but contains the coding sequence for chloramphenicol acetyltransferase (CAT) instead of the sequence for VEGF (Kass-Eisler et al., *Proc. Natl. Acad. Sci.*, 90, 11498–502 (1993)). AdCMV.Null (which is similar to AdCMV.VEGF, but contains no gene in the expression cassette) was used as a control vector (Williams et al., *J. Vasc. Surg.*, 19, 916–923 (1994)).

With respect to construction of AdCMV.VEGF, the cDNA for VEGF$_{165}$ including the signal sequence for secretion (Conn et al., *Proc. Natl. Acad. Sci.*, 87, 2628–32 (1990)) was inserted into an expression plasmid (Mühlhauser et al. (1995), supra) such that the cDNA was placed under the control of the constitutive CMV immediate early promoter/enhancer. The expression plasmid also contains the Ad5 sequence from nucleotide 3384 to nucleotide 5778 (i.e., 9.24 to 16.05 map units), which serves as the homologous recombination sequence. The plasmid carrying the CDNA for VEGF$_{165}$ was cotransfected with the plasmid pJM17 (from F. Graham) into 293 cells (ATCC CRL1573; a human embryonic kidney cell line which has been transformed by Ad5 and expresses the E1 region in trans). The plasmid pJM17 contains the full length Ad5 DNA (36 kb) and PBRX, a 4.3 kb insert placed in the E1 region, thus exceeding by approximately 2 kb the maximum packaging limit of DNA into the adenoviral capsid (McGrory et al., *Virology*, 163, 614–17 (1988)). Homologous recombination between the expression plasmid and pJM17 in 293 cells resulted in replacement of the E1 region and pBRX insert with the expression cassette from the expression plasmid. Ad.RSVβgal and AdCMVCAT were similarly prepared.

The growth of these E1-deleted adenoviruses is limited to 293 cells. For these experiments, 293 cells transduced with the various vectors were propagated in Improved Minimal Essential Medium (IMEM) with 10% heat inactivated fetal bovine serum (FBS), 2 mM glutamine, 50 U/ml penicillin, and 50 μg/ml streptomycin (all from Biofluids, Rockville, Md.). Following cotransfection, individual viral plaques were isolated and amplified in 293 cells, and were purified by CsCl density purification as previously described (Rosenfeld et al., supra). Subsequently, the preparations were dialyzed and stored in dialysis buffer (10 mM Tris-HCl, 1 mM MgCl$_2$, pH 7.4) with 10% glycerol at −70 °C. The titer of each viral stock was determined by plaque assay in 293 cells as previously described; titers consistently ranged between $5 \times 10^9$ and $2 \times 10^{11}$ pfu/ml.

Example 2

This example describes adenoviral-mediated gene transfer to adipocyte tissue in vivo.

Male Sprague-Dawley rats (250 to 300 gm) were used for all studies; all procedures and care of animals were in accordance with institutional guidelines. Animals were anesthetized with intramuscular ketamine (100 mg/kg) and xylazine (2 mg/kg), and a midline laparotomy was performed under sterile conditions. The intestines were displaced to the contralateral side of the abdomen and the retroperitoneal fat was identified. The side of vector administration (right vs. left) was determined pre-operatively in a randomized fashion. A single 6-0 non-absorbable monofilament suture was placed in the center of the adipose tissue to mark the site of injection. The adenoviral vector was administered in a volume of 50 μl using a 0.5 ml syringe with a 30 gauge needle. The needle tip was positioned at a depth of 5 mm from the surface of the fat to achieve uniform delivery, evident by the appearance of a small weal. Sham-treated animals had identifying sutures placed, but no vector administration. The intestines were returned to their normal position and the abdomen was closed in a single layer with non-absorbable suture.

Rats were infected with $2.2 \times 10^9$ pfu of Ad.RSVβgal, and 48 hours later the animals were sacrificed. Sections of rat retroperitoneal adipose tissue were removed and fixed in 4% formalin for 3 hours at 4° C. Gene transfer, in particular, the presence of the lacZ gene product encoded by the β-galactosidase reporter gene, was determined by staining cells with the X-gal reagent (5-bromo-4-chloro-3-indolyl-β-D-galactopyranoside, Boehringer Mannheim Corp., Indianapolis, Ind.), as previously described (Setoguchi et al., supra; Mastrangeli et al., supra). Expression of the lacZ gene product was considered positive when the cells stained blue, particularly in the region of the nucleus. Following infection with Ad.RSVβgal, adipocytes stained blue and were visualized (100×) and photomicrographed as darkened regions of the tissue sample. In comparison, non-infected cells did not demonstrate blue staining, and β-galactosidase was not evident in AdCMV.Null treated and naive (untreated) animals. These results confirm that the transfer of the β-galactosidase reporter gene, and the subsequent expression of this gene, occurred in adipocytes in vivo.

In similar experiments, AdCMVCAT also was delivered to rat retroperitoneal adipose tissue in vivo. Specifically, AdCMVCAT in a total volume of 100 μl in doses of 0, $10^4$, $10^5$, $10^6$, $10^7$, $10^8$, and $10^9$ pfu was injected into rat adipose tissue (n=3 animals/dose). The tissue was harvested after 48 hours, and chloramphenicol acetyltransferase (CAT) levels were quantified by thin layer chromatography and phosphorimager analysis (Kass-Eisler et al., supra). The relative CAT activity was reported as percent conversion of chloramphenicol to its acetylated counterpart by chloramphenicol acetyl transferase.

These results (as depicted in FIG. 1) demonstrate a higher conversion rate with injection of a higher dose of AdCMVCAT. This presumably is due to increased gene transfer with higher multiplicities of infection. Moreover, the results confirm the transfer of the chloramphenicol acetyl transferase reporter gene to adipocytes in vivo. The fact that the graph peaks at a dose of $10^7$ is a function of the assay becoming saturated at this dose. It is likely that even higher levels of CAT production would be detected at the higher doses but for this saturation.

Figure 2:
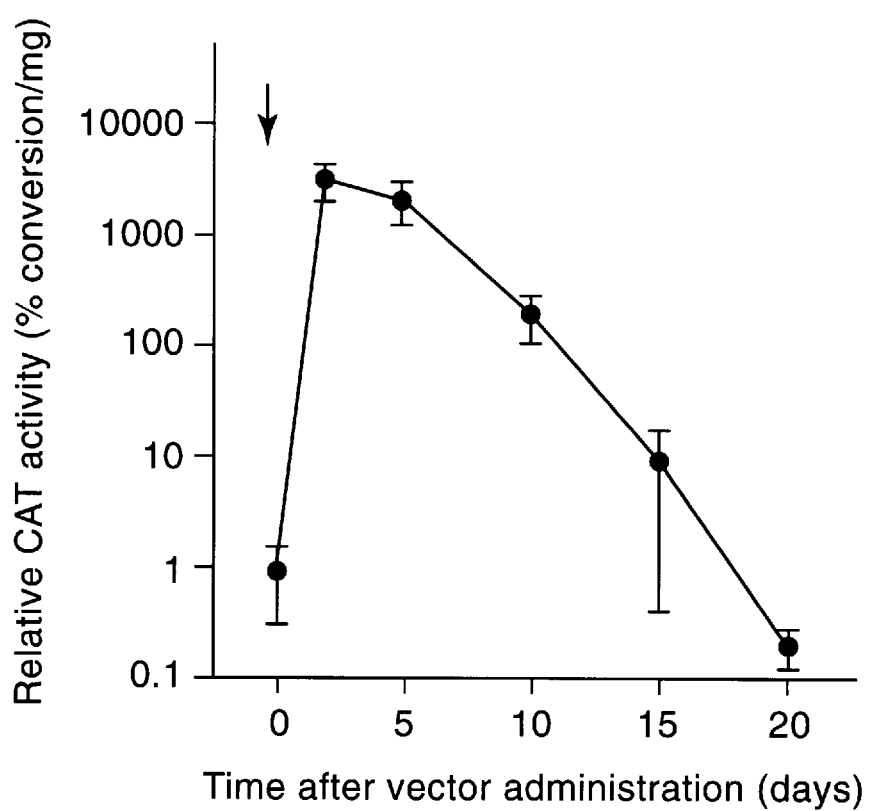
FIG. 2 is a graph of time (days) following vector (AdCMVCAT) administration to rat retroperitoneal adipose tissue versus relative CAT activity (% conversion/mg protein). The arrow indicates the time of vector administration.

Furthermore, a time course experiment demonstrated that chloramphenicol acetyl transferase activity can be detected at high levels for up to 7 days following gene transfer, and at lower levels for up to 10 days following gene transfer (FIG. 2). For this experiment, about 109 pfu/50 μl AdCMVCAT was delivered to rat retroperitoneal fat. The animals were sacrificed at the indicated times, and CAT assays were performed. The values were determined as percent CAT conversion, which either was or was not normalized to mg protein. Three animals were sacrificed per condition at each time point.

The VEGF gene encoded by the AdCMV.VEGF vector also was delivered in vivo to rats. Specifically, rat adipose tissue was injected with either $10^{11}$ pfu of AdCMV.VEGF or with 50 ng of recombinant human VEGF as a positive control. Rat adipose tissue also was injected with $10^{11}$ pfu of Ad.RSVβgal as a negative control. Within 24 hours following gene transfer, rat adipose tissue was excised, minced, and bathed in Dulbecco's modified Eagle medium (2 ml/g tissue) for 6 hours at 37° C. Aliquots (25 μl) of the medium in which the cells were grown were separated on a 15% polyacrylamide gel under reducing conditions, transferred to a nitrocellulose membrane, and assayed by standard Western immunoassay procedures using polyclonal antibodies to the first 20 amino acids of the mature human VEGF N-terminus (Tischer et al., *J. Biol. Chem.*, 266, 11947–54 (1991)) with the peptide being conjugated to a carrier protein, keyhole limpet hemocyanin, using 0.2% glutaraldehyde at a 1:500 dilution and secondary antibody biotinylated for use with a streptavidinalkaline phosphatase conjugate (goat anti-rabbit IgG Bio-Rad Laboratories, Inc., Hercules, Calif.) at a 1:10000 dilution. The results of the Western assay confirm the transfer of the VEGF gene encoded by the AdCMV.VEGF vector to rat adipocytes in vivo, and the production of $VEGF_{165}$ protein by the host adipocytes—i.e., a proper size VEGF protein band was observed with use of the positive control recombinant VEGF, and upon introduction of AdCMV.VEGF, but not upon introduction of Ad.RSVβgal.

The amount of VEGF protein produced was quantified using an enzyme-linked immunoassay (ELISA) for the detection of human VEGF protein (Cytokit Red VEGF enzyme immunoassay, CytImmune Sciences, College Park, Md.). Rat retroperitoneal fat was injected with either the control negative vector AdNull ($10^{11}$particles/50 μl) or AdCMV.VEGF ($10^{11}$ particles/50 μl). The animals were sacrificed immediately, or 1, 2, 5, 10 or 20 days following vector administration. The fat was excised, minced, and bathed in Dulbecco's Modified Eagle Medium (2 ml/gm tissue) for 6 hours at 37° C. to allow release of secreted proteins from the tissue into the medium. Aliquots (25 μl) of the tissue culture medium were loaded into 96-well plates in preparation for the ELISA. The assay was performed according to the manufacturer's instructions, and VEGF concentration was normalized to mg protein. Two animals were sacrificed per condition at each time point. CAT assays were carried out in triplicate.

Figure 3:
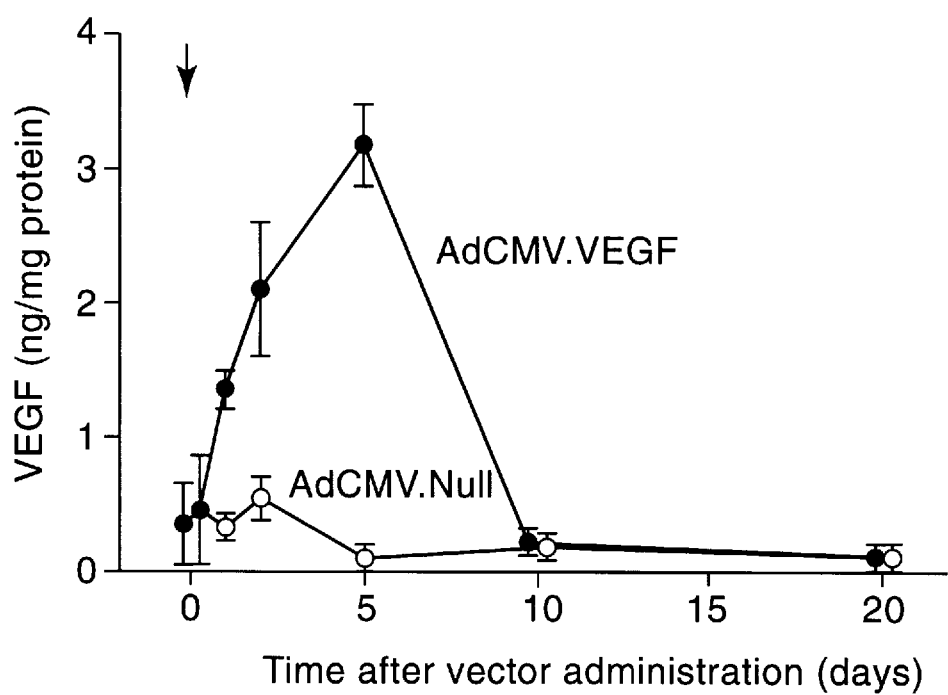
FIG. 3 is a graph of time (days) versus level of VEGF (ng/mg protein) following AdCMV.VEGF (●) or AdCMV.Null (○) administration to rat retroperitoneal tissue. The arrow indicates the time of vector administration.

As can be seen in FIG. 3, quantification of VEGF expression in adipose tissue over time confirmed that the administration of AdCMV.Null did not result in significantly increased levels of VEGF over baseline at any of the time points examined. In comparison, the administration of AdCMV.VEGF resulted in a more than 6-fold increase over baseline VEGF expression, with peak expression occurring about 5 days following vector administration. By day 10, VEGF levels had returned to baseline. The levels of VEGF in these tissues at 1, 2, and 5 days following AdCMV.VEGF administration were significantly greater than the VEGF levels in tissue following administration of AdCMV.Null (p<0.05, each time point). The levels of VEGF on day 0, obtained immediately following vector administration, were similar to the levels in naive animals, which confirms that the viral preparation was not contaminated with VEGF protein (p>0.8). No increase over baseline levels of VEGF was detected in the serum of treated animals, consistent with the observation that adenoviral vector delivery provides a localized gene transfer strategy.

Immunohistochemical staining of adipose tissue was carried out to confirm the presence of VEGF protein 48 hours following administration of AdCMV.VEGF. For these experiments, paraffin sections on slides were blocked with 1.5% goat serum for 20 minutes to prevent nonspecific binding, and were then exposed to primary antibody (rabbit anti-human VEGF; Santa Cruz Biotechnology) at a concentration of 1 µg/ml for 1 hour. A negative control antibody, rabbit polyclonal anti-chloramphenicol acetyl transferase (5'→3', Boulder, Colo.), was applied to a replicate section of each tissue at the same concentration. The test and control antibodies were diluted with phosphate buffered saline (PBS). The primary antibody was eliminated from a parallel slide as an assay control. The slides were exposed sequentially (30 minutes each) with biotinylated goat anti-rabbit IgG (affinity purified against rat serum proteins), ABC reagents (Vector Laboratories, Burlingame, Colo.), and diaminobenzidime (4 minutes) as a substrate for the peroxidase reaction, and were then counterstained with hematoxylin.

The immunohistochemical staining of adipose tissue confirmed the presence of VEGF in the cytoplasm of adipocytes and endothelial cells in AdCMV.VEGF treated tissue, and its absence in AdCMV.Null treated tissue.

Tissue sections were examined 10 days following gene transfer in vivo to determine whether the encoded VEGF gene product exerted any effect on vascularity. Two strategies were used to determine whether the administration of AdCMV.VEGF to retroperitoneal adipose tissue evoked angiogenesis in the adipose tissue: (1) quantification of blood vessels assessed at the macroscopic level (30× magnification) in vivo in living tissue, and (2) quantification of blood vessels<20 µm by histology. All studies were carried out using vector doses of $10^9$ pfu. Control groups included: injected retroperitoneal adipose tissue immediately after injection; retroperitoneal adipose tissue on the contralateral, untreated side; sham-injected adipose tissue; and retroperitoneal adipose tissue injected with the AdCMV.Null control vector.

The quantification of the number of macroscopic blood vessels in living tissue was accomplished by injecting retroperitoneal adipose tissue with AdCMV.VEGF (minimum of 3 animals per time point) or AdCMV.Null (minimum of 3 animals per time point) as described above. Immediately after, and 5, 10, 20, and 30 days following vector administration, the animals were anesthetized, the retroperitoneal adipose tissue was exposed, and injected (ipsilateral) and uninjected (contralateral) tissues were examined in situ under a dissecting microscope (Nikon SMZ-U, Morrell Instrument Co., Inc., Melville, N.Y.) at a distance of 15 cm (×30). Photographic slides were prepared (Ektachrome 64T; Kodak, Rochester, N.Y.), and the slides projected onto a screen at 3 m. Using the identifying suture as the center, a circle was drawn on the screen around the suture with a diameter that corresponded to a distance of 1 cm in situ. The number of vessels that crossed the circle were counted by 3 blinded observers, with a minimum of three vessels counted per slide per observer. The mean of these 3 counts was reported as the number of macroscopic blood vessels in the 1 cm diameter circle of adipose tissue for each animal at each time point.

To quantify the number of vessels<20 µm in the adipose tissue, 1 $cm^3$ samples of both the ipsilateral (treated) retroperitoneal adipose tissue centered around the identifying suture and the contralateral (untreated) adipose tissue were harvested from the same groups of animals used for gross vessel quantification. Tissue was rinsed in PBS and stored in 4% formalin at 4° C. Samples were embedded in paraffin, and serial, 5 µm cross-sections in a plane, parallel to the surface of the tissue, were obtained at intervals of 50 µm.

Three sections were counterstained with hematoxylin and eosin, and 3 sections were counterstained with Masson's trichrome. Random fields were generated by computer, and sections were examined at a magnification of ×400 in a blinded fashion, by a pathologist not associated with the study. Five fields were counted per slide, with a minimum of 4 vessels<20 µm counted per field; 6 slides were evaluated per animal. The counts were averaged, and reported as vessel number per $mm^2$. Results were reported as mean ± standard error of the mean. Statistical analysis was performed by the unpaired two-tailed Student's t-test.

Figure 4:
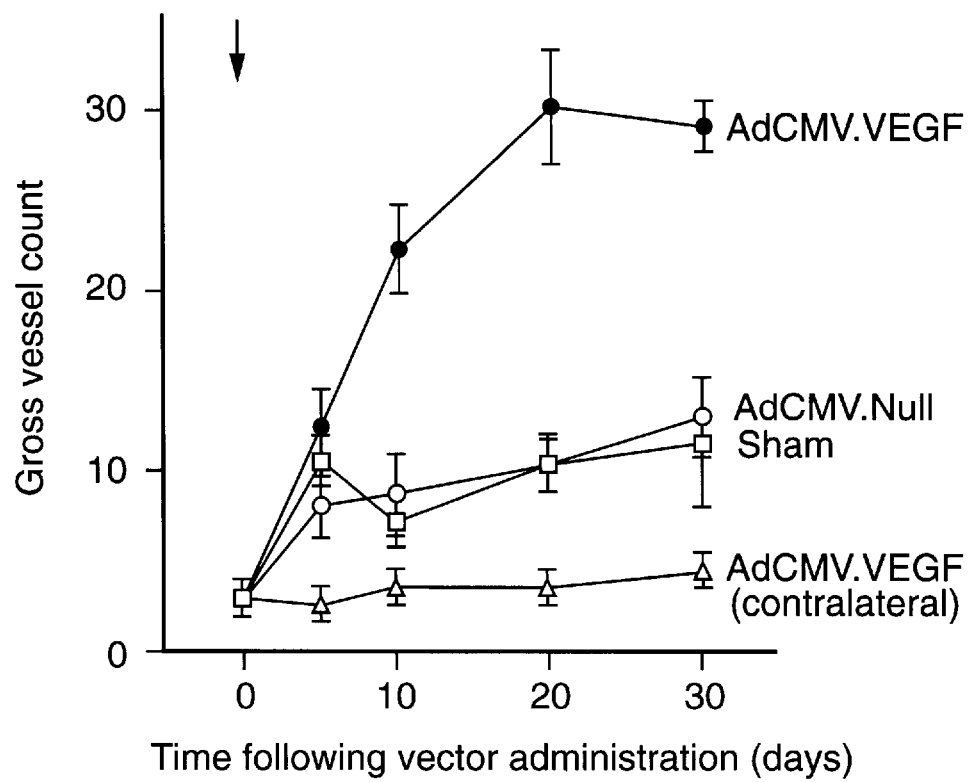
FIG. 4 is a graph of time (days) versus gross vessel count following AdCMV.VEGF (●), AdCMV.Null (○), sham (□) or AdCMV.VEGF (contralateral) (Δ) administration to rat retroperitoneal tissue. The arrow indicates the time of vector administration.

Enhanced vascularity was observed (100× and 600× magnification) following delivery of $10^{11}$ pfu of AdCMV.VEGF to rat retroperitoneal adipose tissue, but not following delivery of $10^{11}$ pfu of Ad.RSVβgal. Similarly, photomicrographs taken in vivo of retroperitoneal adipose tissue demonstrated a marked increase in vascularity at longer times following administration of AdCMV.VEGF. In particular, evaluation 30 days after AdCMV.VEGF administration showed several-fold more vessels in adipose tissue as compared to adipose tissue of naive animals, animals receiving the control AdCMV.Null vector, and the contralateral (untreated) adipose tissue of animals receiving the AdCMV.VEGF vector to the opposite side. Quantitative assessment of the vessel number showed an increase in the number of blood vessels in the adipose tissue 10 days after the administration of AdcMV.VEGF which was 667% that of the uninjected contralateral control adipose tissue in the same animals, and 310% and 256% that of the sham and AdCMV.Null control adipose tissue (p<0.01, all comparisons, FIG. 4). Importantly, the increase in the quantitative in vivo blood vessel counts were maintained in the adipose tissue 20 and 30 days following vector administration (p<0.004, all comparisons), despite the fact that VEGF could not be detected in the adipose tissue at day 10 following administration of the AdCMV.VEGF.

Figure 5:
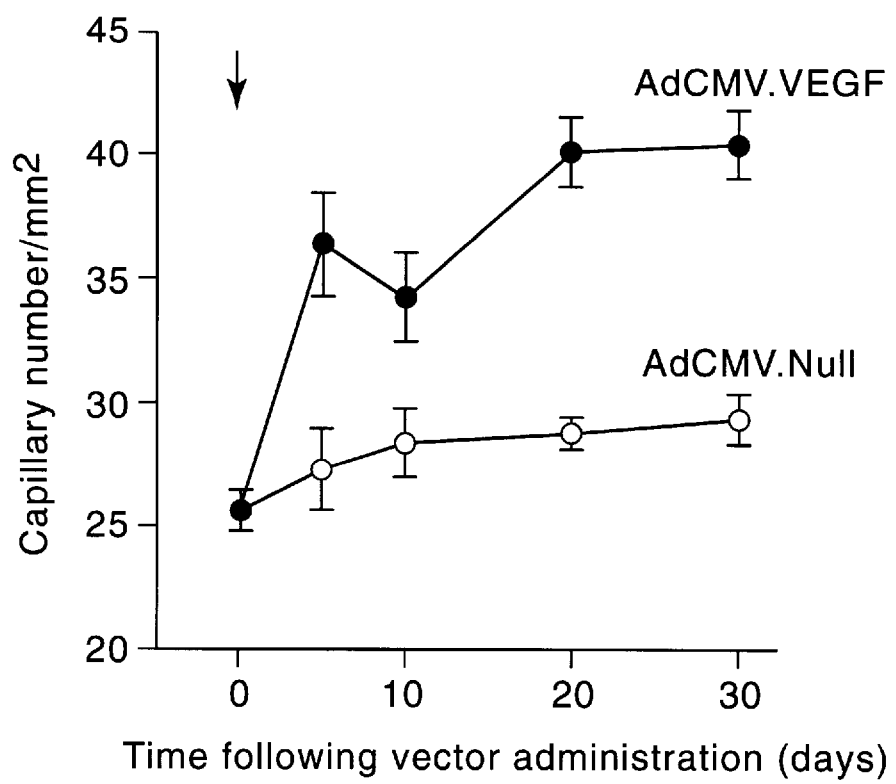
FIG. 5 is a graph of time (days) versus capillary number/$mm^2$ following AdCMV.VEGF (●) or AdCMV.Null (○) administration ($10^9$ pfu) to rat retroperitoneal tissue. The arrow indicates the time of vector administration.

Histologic evaluation of capillary number was consistent with the observations made of in vivo blood vessel quantification. For these experiments, all samples were examined at a magnification of 400×, and were counterstained with α-actin. In the AdCMV.VEGF-injected tissue, histologic evaluation showed more capillaries 30 days after vector administration compared to the naive and AdCMV.Null-injected controls, as well as the contralateral (untreated) adipose tissue of an animal injected with the AdCMV.VEGF vector. Quantitative assessment of the histologic samples (FIG. 5) showed a 21 to 39% increase in capillary number in the AdCMV.VEGF-injected adipose tissue compared to the AdCMV.Null controls at days 5, 10, 20, and 30 (p<0.0002, all comparisons), i.e., as with the in vivo blood vessel quantification of vessels observed at 30× magnification, there was persistence in the increased capillary number despite the fact that VEGF could not be detected at day 10 and thereafter.

These results confirm that adenoviral-mediated gene transfer to adipocytes in vivo can be employed to attain a therapeutic effect. In particular, the results validate that an adenoviral vector carrying the VEGF cDNA is capable of inducing the growth of new blood vessels in a regional fashion in a relatively avascular, normal organ. This indicates that in vivo adenoviral-mediated gene transfer can be used inter alia for therapeutic angiogenesis, for instance, in the treatment of ischemic cardiovascular disease.

All of the references cited herein, including patents, patent applications, and publications, are hereby incorporated in their entireties by reference.

While this invention has been described with an emphasis upon preferred embodiments, it will be obvious to those of ordinary skill in the art that variations in the preferred embodiments can be used, including variations due to improvements in the art, and that the invention can be practiced otherwise than as specifically described herein. Accordingly, this invention includes all modifications encompassed within the spirit and scope of the invention as defined by the following claims.

What is claimed is:

1. A method of increasing the vascularity of adipose tissue which comprises contacting said adipose tissue with an adenoviral vector comprising a promoter and, operably linked thereto, a DNA encoding an angiogenic protein such that said adenoviral vector enters said adipose tissue, said angiogenic protein is produced, and said adipose tissue has an increased vascularity.

2. The method of claim 1, wherein said adenoviral vector is replication-deficient.

3. The method of claim 1, wherein said promoter is an adipocyte-specific promoter.

4. The method of claim 3, wherein said promoter is selected from the group consisting of the aP2 gene regulatory region and the p154 polypeptide gene regulatory region.

5. The method of claim 1, wherein said promoter is a constitutive promoter.

6. The method of claim 1, wherein said adipose tissue is transferred to another site with a host.

7. The method of claim 6, wherein said DNA encodes a vascular endothelial growth factor.

8. Isolated adipose tissue comprising an adenoviral vector comprising a promoter and, operably linked thereto, a DNA encoding an angiogenic protein, characterized in that when said adipose tissue is implanted in vivo an increase in the vascularity of said adipose tissue occurs.

9. The isolated adipose tissue of claim 8, wherein said vector is replication deficient.

10. The isolated adipose tissue of claim 8, wherein said DNA encodes a vascular endothelial growth factor.

* * * * *